(12) United States Patent
Liebig et al.

(10) Patent No.: US 10,618,867 B2
(45) Date of Patent: Apr. 14, 2020

(54) METHOD FOR PRODUCING SURFACTANTS

(71) Applicant: Evonik Degussa GmbH, Essen (DE)

(72) Inventors: Stefan Julian Liebig, Düsseldorf (DE); Dominik Schuch, Düsseldorf (DE); Jan Marian von Hof, Bochum (DE); Kathrin Daniela Brandt, Düsseldorf (DE); Maximilian Vogt, Essen (DE); Hans Henning Wenk, Mülheim an der Ruhr (DE)

(73) Assignee: Evonik Operations GmbH, Essen (DE)

(*) Notice: Subject to any disclaimer, the term of this patent is extended or adjusted under 35 U.S.C. 154(b) by 0 days.

(21) Appl. No.: 16/312,480

(22) PCT Filed: Jun. 6, 2017

(86) PCT No.: PCT/EP2017/063668
§ 371 (c)(1),
(2) Date: Dec. 21, 2018

(87) PCT Pub. No.: WO2018/001680
PCT Pub. Date: Jan. 4, 2018

(65) Prior Publication Data
US 2019/0135734 A1 May 9, 2019

(30) Foreign Application Priority Data
Jun. 29, 2016 (EP) .................................. 16176790

(51) Int. Cl.
| C07C 231/02 | (2006.01) |
| C07C 231/12 | (2006.01) |
| C07C 233/36 | (2006.01) |
| C07C 233/49 | (2006.01) |
| A61K 8/44   | (2006.01) |

(52) U.S. Cl.
CPC .......... *C07C 231/02* (2013.01); *C07C 231/12* (2013.01); *C07C 233/36* (2013.01); *C07C 233/49* (2013.01); *A61K 8/442* (2013.01)

(58) Field of Classification Search
CPC ... C07C 231/02; C07C 231/12; C07C 233/36; C07C 233/49; A61K 8/442
USPC ........................................................ 554/69
See application file for complete search history.

(56) References Cited

U.S. PATENT DOCUMENTS

| 3,694,451 A | 9/1972 | Mihailovski |
| 3,836,551 A | 9/1974 | Uddrich et al. |
| 4,380,646 A | 4/1983 | Franzmann |
| 4,772,424 A | 9/1988 | Greeb |
| 5,856,538 A | 1/1999 | Strecker et al. |
| 5,898,084 A | 4/1999 | Oftring et al. |
| 6,703,517 B2 | 3/2004 | Hattori et al. |
| 7,439,388 B2 | 10/2008 | Harichion et al. |
| 8,138,372 B2 | 3/2012 | Herrwerth et al. |
| 8,263,538 B2 | 9/2012 | Tsaur et al. |
| 9,776,951 B2 | 10/2017 | Friedrich et al. |
| 9,890,107 B2 | 2/2018 | Schuch et al. |
| 9,963,425 B2 | 5/2018 | Jaworska-Maslanka et al. |
| 2005/0027120 A1 | 2/2005 | Gojon-Zorrilla |
| 2008/0108709 A1 | 5/2008 | Meyer et al. |
| 2011/0206623 A1 | 8/2011 | Wenk et al. |
| 2015/0141466 A1 | 5/2015 | Klug et al. |
| 2015/0335555 A1 | 11/2015 | Dobrowolski et al. |
| 2016/0083333 A1 | 3/2016 | Schwab et al. |
| 2017/0202770 A1 | 7/2017 | Friedrich et al. |
| 2017/0218120 A1 | 8/2017 | Brandt et al. |
| 2017/0306264 A1 | 10/2017 | Peggau et al. |
| 2017/0335238 A1 | 11/2017 | Schilling et al. |
| 2018/0016525 A1 | 1/2018 | Scheuermann et al. |
| 2018/0023040 A1 | 1/2018 | Schilling et al. |
| 2018/0036218 A1 | 2/2018 | Gu et al. |
| 2018/0344602 A1 | 12/2018 | Schuch et al. |

FOREIGN PATENT DOCUMENTS

| DE | 2004099 A1 | 8/1971 | |
| DE | 4408957 A1 | 9/1995 | |
| EP | 0656346 A1 * | 6/1995 | ............. A61K 8/442 |
| EP | 0656346 A1 | 6/1995 | |
| EP | 1672055 A1 | 6/2006 | |
| GB | 1337782 A * | 11/1973 | ........... C07C 231/02 |
| JP | S57/58653 | 4/1982 | |
| WO | 9507881 A1 | 3/1995 | |
| WO | 2008019887 A2 | 2/2008 | |
| WO | 2013014264 A1 | 1/2013 | |
| WO | 2013014265 A1 | 1/2013 | |
| WO | 2013014266 A1 | 1/2013 | |
| WO | 2013014267 A1 | 1/2013 | |
| WO | 2013014268 A1 | 1/2013 | |
| WO | 2014008103 A1 | 1/2014 | |

OTHER PUBLICATIONS

German language Written Opinion dated Aug. 9, 2017 in PCT/EP2017/063668 (5 pages).
International Search Report dated Aug. 9, 2017 in PCT/EP2017/063668 (2 pages).
Lu et al., U.S. Appl. No. 16/074,828, filed Aug. 2, 2018.

* cited by examiner

*Primary Examiner* — Deborah D Carr
(74) *Attorney, Agent, or Firm* — Nexsen Pruet PLLC; Philip P. McCann

(57) ABSTRACT

The present invention relates to a method in which an amino acid is reacted with an acyl group donor to obtain an N-acylamino acid in the presence of an amine.

20 Claims, No Drawings

METHOD FOR PRODUCING SURFACTANTS

CROSS REFERENCE TO RELATED APPLICATIONS

This application is a 35 U.S.C. § 371 U.S. national phase entry of International Application No. PCT/EP2017/063668 having an international filing date of Jun. 6, 2017, which claims the benefit of European Application No. 16176790.0 filed Jun. 29, 2016, each of which is incorporated herein by reference in its entirety.

FIELD

The present invention relates to a method in which an amino acid is reacted with an acyl group donor to obtain an N-acylamino acid in the presence of an amine.

BACKGROUND

N-acylamino acids are particularly mild anionic surfactants and are therefore known as interesting ingredients for cosmetic formulations. A broader use however involves a complex manufacturing process and high costs linked thereto.

Amphosurfactants, such as betaines in particular, form an important element of cosmetic formulations and are known for the formation of a thick, soft foam having a high stability. Furthermore, due to their good biodegradability and low toxicity, they are used in large amounts in the cosmetic industry. Amphoteric surfactants are also known for their mildness and as amphoteric surfactants they may form strong synergies with anionic surfactants such as SLS or SLES. For this reason, SLES/betaine surfactant mixtures form the market standard.

The synergies between amphosurfactants and anionic surfactants may be of a different nature and, for example, influence the thickening, the foam behavior or the mildness of a mixture. Typical cosmetic formulations which contain both N-acylamino acids and betaines are also present on the market. These correspond to the present trend to develop sulphate-free and PEG-free formulations.

U.S. Pat. No. 8,263,538 discloses the use of N-acylamino acids in combination with amphoteric/zwitterionic surfactants in order to achieve a very mild formulation.

US20150335555 discloses the composition of a sulphate-free cosmetic formulation consisting of zwitterionic/amphoteric surfactants, N-acylglycinates and non-ionic surfactants.

US20150141466 discloses the use of amino acid surfactants and betaines in combination with N-methyl-N-acylglucamines.

U.S. Pat. No. 4,772,424 discloses a formulation comprising a specific composition of sulphate/sulphonate, betaine and sarcosinate in order to obtain an isotropic mixture.

N-acylamino acids are currently commercially obtained exclusively from acid chlorides and amino acids by the Schotten-Baumann reaction, as disclosed in U.S. Pat. No. 6,703,517 for example. Acid chlorides are prepared by toxic chlorinating agents, generating a waste stream, which cam make the acid chlorides thus obtained relatively expensive precursors. The chlorinating agents used, such as phosphorus chlorides for example, are prepared in energy-intensive and environmentally harmful processes.

In the Schotten-Baumann route, stoichiometric amounts of NaCl are formed, which remain in the product mixture.

Oxidation reactions of amidoalcohols to N-acylamino acids have been disclosed by a TEMPO catalyzed method in U.S. Pat. No. 7,439,388 and by heterogeneous catalysis in WO2008019887. The yields and selectivities of this method and the use of expensive catalysts render this method unattractive.

Furthermore, the direct synthesis of N-acylamino acids from fatty acids and amino acids has been disclosed in EP1672055, U.S. Pat. No. 3,836,551, DE4408957. In this method, by-products such as di-, tri- or tetrapeptides often occur, high temperatures are required, the ratio of fatty acids to amino acids is in some cases unfavorable or the use of solvents is necessary.

The preparation of N-acylamino acids is also possible from fatty acid esters (alkyl esters or polyol esters), such as disclosed in U.S. Pat. No. 5,856,538, WO9507881, DE4408957, U.S. Pat. Nos. 4,380,646, 5,898,084, JP57/058653 and US20050027120. Both starting compounds are incompatible due to their polarities and, when reaction is successful, the product solidifes and cannot be melted without decomposition. In the cases of secondary components separation by distillation, such as in the example of methanol in the case of methyl esters, strong foaming can occur. By-products are formed and, in the case of the use of a solvent, the removal thereof is difficult.

The N-acylation method may be carried out by using a polyol, such as for example glycerol, as reaction medium. This means that the solidified product can be further stirred during the reaction. The glycerol remains in the product mixture after the reaction; see in this case WO2013014264, WO2013014265, WO2013014266, WO2013014267 and WO2013014268. In this method, a solid concentrate mainly consisting of N-acylamino acid and glycerol is obtained. WO2014008103 discloses another method in which an aqueous solution of N-acylamino acid is obtained.

SUMMARY

The object of the invention was to provide a method for preparing surfactants in which at least one of the disadvantages of the prior art is overcome.

DESCRIPTION OF THE INVENTION

Surprisingly, it has been found that the method described hereinafter is able to solve the problem posed by the invention.

The present invention relates to a method comprising the method steps of
A) providing a mixture comprising an amino acid and an amine selected from at least one of the group consisting of amidamines and trialkylamines and
B) reacting the amino acid with an acyl group donor to obtain an N-acylamino acid.

An advantage of the present invention is that the surfactant obtained by the method according to the invention comprises only very low amounts, if any at all, of free glycerol. Large amounts of glycerol in cosmetic formulations are undesirable since these negatively influence, for example, the thickenability of cosmetic formulations.

A further advantage of the present invention is that the surfactants obtained by the method according to the invention comprise only very low amounts, if any at all, of NaCl. This is of advantage since relatively high amounts of NaCl may have a corrosive effect and since electrolytes are undesirable in some formulations.

Another advantage of the present invention is that large amounts of basic metal catalyst are not used, which remain in the surfactant and have to possibly be later neutralized.

A further advantage of the present invention is that the surfactants obtained by the method according to the invention comprise only very little oligopeptidic by-products.

Another advantage of the present invention is that the method according to the invention can be carried out at relatively low temperatures and can therefore be carried out in an energetically favorable manner.

A further advantage is that the method according to the invention is more environmentally friendly, less hazardous and more cost-effective compared to standard methods by the Schotten-Baumann route.

A further advantage of the method according to the invention is that, for example, cocoyl glyinate can be prepared from various esters and triglycerides having different carbon chain distributions, particularly also comprising unsaturated acyl radicals which are not accessible by the Schotten-Baumann route. This can also have a positive effect on the thickening properties in cosmetic formulations.

A further advantage is that the amine in method step A) acts as a basic solvent whereby the reaction is additionally catalyzed.

A further advantage is that the product mixture prepared by the method according to the invention from acylamino acid and amphosurfactant can be prepared at significantly higher concentrations in aqueous solution than a pure acylamino acid, whereby, inter alia, transport costs can be saved.

A further advantage is that the acylamino acid for the amine in method step A) functions as solubilizer in aqeuous solution, whereby a subsequent betainization can effectively be carried out.

The method according to the invention is particularly suitable for preparing surfactants, in particular N-acylamino acids.

In the context of the present invention, the term "acid" always also includes the corresponding salt of the acid. This also applies in particular to the terms "amino acid" and "N-acylamino acid". In the context of the present invention, the term "amino acid" is understood to mean a compound having an optionally protonated $NH_2$ group and an optionally deprotonated Brønsted acid group, in particular a carboxylate or sulphonate group, wherein a carboxylate group is particularly preferred.

In the context of the present invention, the term "amidamine" is understood to mean an optionally protonated primary, secondary or tertiary amine having an amide group, Unless stated otherwise, all percentages (%) given are percentages by mass.

A method is claimed comprising the method steps of
A) providing a mixture comprising an amino acid and an amine selected from at least one of the group consisting of amidamines and trialkylamines and
B) reacting the amino acid with an acyl group donor to obtain an N-acylamino acid.

It is also evident that in each case several of the individual components (amino acid, amidamine, trialkylamine and acyl group donor) can be used in the form of technical mixtures, for example.

The amino acid present in the mixture provided in method step A is preferably provided in the form of an aqueous solution.

The water additionally present in the mixture provided in method step A) preferably has a pH in a range of 7 to 14, preferably 9 to 13. The pH is adjusted in accordance with the invention preferably by the addition of ammonia, basic alkaline earth metal or alkali metal salts, particularly preferably hydroxides, especially preferably KOH or NaOH. In this context, it is particularly preferable that the water additionally present in the mixture provided in method step A) has an alkaline earth metal or alkali metal hydroxide concentration of 1.0 to 4.0, preferably 1.01 to 2.5 mole equivalents, based on the amino acid. This has the consequence that the amino acid provided in method step A) is predominantly present in the form of its salt.

The amino acid provided in method step A) is preferably selected in accordance with the invention from the group comprising peptides, oligopeptides, proteinogenic amino acids, non-proteinogenic aminocarboxylic acids and aminosulphonic acids.

Non-proteinogenic aminocarboxylic acids preferably used in accordance with the invention in method step A) are selected from L-thyroxine, 2,6-diaminopimelic acid, L-azetidine-2-carboxylic acid, sarcosine, homoserine, lanthionine, djenkolic acid, cystathionine, L-homocysteine, ethionine, δ-aminolevulinic acid, 4-aminobenzoic acid, dehydroalanine, GABA, 3-aminoisobutyric acid, L-homoserine, L-ornithine, L-citrulline, argininosuccinate, L-DOPA, L-5-hydroxytryptophan, β-alanine, β-methylaminoalanine, ibotenic acid, D-valine, D-alanine, D-glutamic acid, hypoglycin, hydroxyproline, norleucine, methyltaurine and taurine, wherein sarcosine, methyltaurine and taurine are particularly preferred.

Proteinogenic amino acids preferably used in accordance with the invention in method step A) are selected from the group of glycine, alanine, valine and glutamic acid.

Amino acids particularly preferably used in accordance with the invention in method step A) are selected from the group of sarcosine, glycine and glutamic acid.

At least one amidamine is preferably used as amine in method step A).

Amidamine preferably used in accordance with the invention in method step A) is selected from those of the general formula 1):

$$\underset{R^1}{\overset{O}{\|}}\underset{|}{\overset{}{C}}-\underset{|}{\overset{}{N}}-\left[\overset{H_2}{C}\right]_n-\underset{|}{\overset{}{N}}-R^3 \qquad \text{general formula 1)}$$
$$\qquad\qquad R^2 \qquad\qquad R^4$$

where $R^1$=optionally hydroxy-substituted, optionally mono- or polyunsaturated alkyl or alkyaryl radicals comprising 5 to 29, preferably 7 to 21, particularly preferably 7 to 17, carbon atoms, where $R^2$=H or alkyl radical comprising 1-3 carbon atoms, preferably H where W and $R^4$=mutually independent, identical or different H or alkyl radicals comprising 1 to 6 carbon atoms, preferably methyl and n=1 to 6, preferably 2 to 3, particularly preferably 3.

Amidamine of the general formula 1) particularly preferably used is selected from those with $R^1CO$ selected from acyl radicals of fatty acids, particularly coconut fatty acids, palm kernel fatty acids, palm fatty acids, rapeseed oil fatty acids. Amidamines derived from such fatty acids are preferably characterized in that $R^2$=H, $R^3$ and $R^4$=methyl and n=3.

Trialkylamine preferably used in accordance with the invention in method step A) is selected from those of the general formula 2):

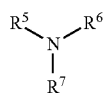

general formula 2)

where $R^5$=optionally hydroxy-substituted, optionally mono- or polyunsaturated alkyl or alkyaryl radicals comprising 6 to 30, preferably 8 to 22, particularly preferably 8 to 18, carbon atoms,
$R^6$ and $R^7$=mutually independent, identical or different alkyl radicals comprising 1 to 6 carbon atoms, preferably methyl.

Since the mixture provided in method step A) additionally comprises water, it is preferred in accordance with the invention that the water for carrying out method step B) is reduced to a content of below 0.5% by weight, in particular below 0.1% by weight, wherein the % by weight refers to the sum total of amino acids, amine and water. The reduction of the water content is preferably carried out by heating to a temperature range of 40° C. to 130° C., preferably 80 to 110° C., wherein it is particularly preferred in accordance with the invention to operate in a pressure range from 0.01 to 1000 mbar, preferably 1 to 400 mbar.

In accordance with the invention, preference is given to using an acyl group donor in method step B) selected from carboxylic esters, preferably esters based on alkanols and polyols having up to 6 carbon atoms, particularly preferably up to 3 carbon atoms, especially preferably glycerol esters.

In accordance with the invention, preference is given to using an acyl group donor in method step B) selected from acyl group donors which provide an acyl group selected from at least one of the group of the acyl groups of fatty acids.

In accordance with the invention, particular preference is given to using an acyl group donor in method step B) selected from natural fats and oils, preferably selected from coconut oil, palm kernel oil and palm oil.

Method step B) according to the invention is preferably carried out in a temperature range from 80° C. to 160° C., preferably 110 to 150° C., wherein it is particularly preferred in accordance with the invention to operate in a pressure range from 1 to 3000 mbar, preferably 900 to 1100 mbar. Method step B) according to the invention is preferably carried out in the presence of a basic catalyst, preferably alkaline earth metal or alkali metal salts, preferably hydroxides, particularly preferably NaOH or KOH.

It is preferred in accordance with the invention if the method according to the invention is characterized in that the components amino acid, amine and the sum total of the acyl groups of the acyl group donors are used in a molar ratio of from 1:100:1 to 100:1:100, preferably from 1:8:1 to 8:1:8, particularly preferably from 1:2:1 to 2:1:2.

The method according to the invention can be completed preferably by the method step C) of betainization of the amine with a halocarboxylic acid.

This method preferred in accordance with the invention comprising method step C) is particularly suitable for preparing surfactant mixtures comprising at least one N-acylamino acid and at least one betaine.

Halocarboxylic acids used in method step C) are understood to mean generally chloro- or bromocarboxylic acids having 2 to 4 carbon atoms, preferably chloroacetic acid or chloropropionic acid, particularly chloroacetic acid. In addition to halocarboxylic acids, it is also possible to use alkali metal salts thereof, preferably sodium salts thereof.

Method step C) is preferably carried out maintaining a pH in the range of 7 to 13, preferably 7.5 to 10.

Method step C) is preferably carried out in a temperature range from 40° C. to 120° C., preferably from 80° C. to 115° C.

Method step C) is preferably carried out up to a free amine content of below 0.5% by weight, wherein the % by weight refers to the total weight of amine used in method step A).

It is preferred in method step C) according to the invention to add water as solvent, in particular in a weight ratio of water to amine of from 1:0.01 to 0.01:1, preferably from 1:0.05 to 1:1, particularly preferably from 1:0.1 to 1:0.6.

The examples adduced hereinafter describe the present invention by way of example, without any intention that the invention, the scope of application of which is apparent from the entirety of the description and the claims, be restricted to the embodiments specified in the examples.

EXAMPLES

Example 1

In a 1 L stirring apparatus equipped with distillation attachment and nitrogen inlet, 133.9 g of a dimethylaminopropylamide of coconut fatty acid (0.46 mol, prepared according to the methods described in EP656346) were added to a solution of 37.5 g of glycine (0.5 mol), 22.4 g of NaOH (0.56 mol) and 67.2 g of water. The mixture was heated to 105° C. under reduced pressure until all the water had been removed from the system. Subsequently, 112.8 g of coconut oil (0.17 mol) were added and the mixture was heated to 145° C. After 4 h reaction time, the conversion according to TLC was complete (n-butanol:acetic acid:water=3:1:1, ninhydrin stain reagent, $R_f$=0.2). The mixture was characterized by NMR spectroscopy and comprised at this time point 45% cocoyl glycinate (confirmed by HPLC: lauroyl glycinate standard).

112.7 g of the reaction material (0.18 mol of cocoyl glycinate, 0.17 mol of amidamine) were dissolved in 268.6 g of water and reacted with 19.9 g of monochloroacetic acid (80% aqueous solution, 0.17 mol) at 50-95° C. according to standard methods and the pH was adjusted to 9.25. After 4 h at 95° C., the content of residual amidamine was below 0.2%. The product was characterized by NMR spectroscopy and the aqueous solution comprised by calculation at this time point 13% cocoyl glycinate (confirmed by HPLC: lauroyl glycinate standard).

Example 2

In accordance with Example 1, 49.5 g of a dimethylaminopropylamide of coconut fatty acid (0.17 mol, prepared according to the known methods described, for example, in EP656346) were added to a solution of 40.5 g of glycine (0.54 mol), 48.6 g of NaOH (0.59 mol) and 72.9 g of water. The mixture was heated to 105° C. under reduced pressure until all the water had been removed from the system. 13.5 g of NaOMe (25% in methanol, 0.05 mol of NaOMe) were added and methanol was evaporated. Subsequently, 121.8 g of coconut oil (0.18 mol) were added and the mixture was heated to 145° C. After 4 h reaction time, the conversion according to TLC was complete (n-butanol:acetic acid:water=3:1:1, ninhydrin stain reagent, $R_f$=0.2).

88.5 g of the reaction material (0.19 mol of cocoyl glycinate, 0.07 mol of amidamine) were dissolved in 88.5 g of water and reacted with a solution of 8.2 g of monochloroacetic acid (80% aqueous solution, 0.07 mol) in 119.5 g of water at 50-95° C. according to standard methods and the pH was adjusted to 9.25. After 4 h at 95° C., the content of residual amidamine was below 0.2%. The product was characterized by NMR spectroscopy and the aqueous solution comprised by calculation at this time point 19% cocoyl glycinate (confirmed by HPLC: lauroyl glycinate standard).

Example 3

In accordance with Example 1, 178.1 g of a dimethylaminopropylamide of coconut fatty acid (0.61 mol, prepared according to the known methods described, for example, in EP656346) were added to a solution of 18.8 g of glycine (0.25 mol), 20 g of NaOH (0.25 mol) and 38.1 g of water. The mixture was heated to 105° C. under reduced pressure until all the water had been removed from the system. Subsequently, 53.6 g of methyl laurate (0.25 mol) were added and the mixture was heated to 130° C. After 4 h reaction time, the conversion according to TLC was complete (n-butanol:acetic acid:water=3:1:1, ninhydrin stain reagent, $R_f$=0.2).

78.9 g of the reaction material (0.07 mol of lauroyl glycinate, 0.16 mol of amidamine) were dissolved in 221.2 g of water and reacted with 18.8 g of monochloroacetic acid (80% aqueous solution, 0.16 mol) at 50-95° C. according to standard methods and the pH was adjusted to 9.25. After 4 h, the content of residual amidamine was below 0.2%. The product was characterized by NMR spectroscopy and the aqueous solution comprised by calculation at this time point 6% lauroyl glycinate (HPLC: lauroyl glycinate standard).

Example 4

In accordance with Example 1, 133.9 g of a dimethylaminopropylamide of coconut fatty acid (0.46 mol, prepared according to the known methods described, for example, in EP656346) were added to a solution of 44.5 g of sarcosine (0.5 mol), 22.4 g of NaOH (0.56 mol) and 67.2 g of water. The mixture was heated to 105° C. under reduced pressure until all the water had been removed from the system. Subsequently, 112.8 g of coconut oil (0.17 mol) were added and the mixture was heated to 145° C. After 4 h reaction time, the conversion according to TLC was complete (n-butanol:acetic acid:water=3:1:1, ninhydrin stain reagent, $R_f$=0.2).

112.7 g of the reaction material (0.18 mol of cocoyl sarcosine, 0.16 mol of amidamine) were dissolved in 268.6 g of water and reacted with 18.9 g of monochloroacetic acid (80% aqueous solution, 0.16 mol) at 50-95° C. according to standard methods and the pH was adjusted to 9.25. After 4 h, the content of residual amidamine was below 0.2%. The product was characterized by NMR spectroscopy and the aqueous solution comprised by calculation at this time point 14% cocoyl sarcosinate.

Example 5

In accordance with Example 1, 133.9 g of a dimethylaminopropylamide of coconut fatty acid (0.46 mol, prepared according to the known methods described, for example, in EP656346) were added to a solution of 60.1 g of glycine (0.8 mol), 35.2 g of NaOH (0.88 mol) and 105.6 g of water. The mixture was heated to 105° C. under reduced pressure until all the water had been removed from the system. Subsequently, 136.2 g of triglycerides of caprylic/capric acid (TEGOSOFT® CT, 0.27 mol) were added and the mixture was heated to 145° C. After 4 h reaction time, the conversion according to TLC was complete (n-butanol:acetic acid:water=3:1:1, ninhydrin stain reagent, $R_f$=0.2).

112.7 g of the reaction material (0.26 mol of capryloyl/caprinoyl glycinate, 0.15 mol of amidamine) were dissolved in 268.6 g of water and reacted with 17.7 g of monochloroacetic acid (80% aqueous solution, 0.15 mol) at 50-95° C. according to standard methods and the pH was adjusted to 9.25. After 4 h, the content of residual amidamine was below 0.2%. The product was characterized by NMR spectroscopy and the aqueous solution comprised by calculation at this time point 14% capryloyl/caprinoyl glycinate.

Example 6

In accordance with Example 1, 64 g of N,N-dimethyldodecylamine (0.3 mol) were added to a solution of 11.3 g of glycine (0.15 mol), 6.8 g of NaOH (0.17 mol) and 20.4 g of water. The mixture was heated to 105° C. under reduced pressure until all the water had been removed from the system. Subsequently, 33.8 g of coconut oil (0.05 mol) were added and the mixture was heated to 145° C. After 4 h reaction time, the conversion according to TLC was complete (n-butanol:acetic acid:water=3:1:1, ninhydrin stain reagent, $R_f$=0.2).

70 g of the reaction material (0.19 mol of cocoyl glycinate, 0.17 mol of N,N-dimethyldodecylamine) were dissolved in 250 g of water and reacted with 20.1 g of monochloroacetic acid (80% aqueous solution, 0.17 mol) at 50-95° C. and the pH was adjusted to 9.25. The product was characterized by NMR spectroscopy and the aqueous solution comprised by calculation at this time point 15% cocoyl glycinate.

Example 7

In accordance with Example 1, 137.1 g of a dimethylaminopropylamide of palm kernel fatty acid (0.46 mol, prepared according to the known methods described, for example, in EP656346) were added to a solution of 37.5 g of glycine (0.5 mol), 31.4 g of KOH (0.56 mol) and 94.1 g of water. The mixture was heated to 105° C. under reduced pressure until all the water had been removed from the system. Subsequently, 113 g of palm kernel fat (0.17 mol) were added and the mixture was heated to 135° C. After 4 h reaction time, the conversion according to TLC was complete (n-butanol:acetic acid:water=3:1:1, ninhydrin stain reagent, $R_f$=0.2).

117.1 g of the reaction material (0.18 mol of cocoyl glycinate, 0.17 mol of amidamine) were dissolved in 268.6 g of water and reacted with 19.9 g of monochloroacetic acid (80% aqueous solution, 0.17 mol) at 50-95° C. according to standard methods and the pH was adjusted to 9.25. After 4 h, the content of residual amidamine was below 0.2%. The product was characterized by NMR spectroscopy and the aqueous solution comprised by calculation at this time point 17% cocoyl glycinate.

Example 8

In accordance with Example 1, 93.2 g of tripropylamine (0.65 mol) were added to a solution of 24.4 g of glycine (0.33 mol), 14.7 g of NaOH (0.37 mol) and 44.3 g of water. The mixture was heated to 110° C. under reduced pressure until all the water had been removed from the system. Subsequently 73.3 g of coconut oil (0.11 mol) were added and the mixture was heated to 145° C. After 4 h reaction time, the conversion according to TLC was incomplete (n-butanol:acetic acid:water=3:1:1, ninhydrin stain reagent, $R_f$=0.2. The product mixture comprised at this time point 1.4% cocoyl glycinate (HPLC: standard lauroyl glycinate). The theoretical value for the proportion of cocoyl glycinate at this time point is 46.6%.

Example 9

In accordance with Example 1, 121.7 g of N,N-dimethyldodecylamine (0.57 mol) were added to a solution of 21.4 g of glycine (0.29 mol), 12.9 g of NaOH (0.32 mol) and 38.8 g of water. The mixture was heated to 105° C. under reduced pressure until all the water had been removed from the system. Subsequently, 55.3 g of coconut fatty acid (0.29 mol) were added and the mixture was heated to 145° C. After 4 h reaction time, the conversion according to TLC was incomplete (n-butanol:acetic acid:water=3:1:1, ninhydrin stain reagent, $R_f$=0.2). The product mixture comprised at this time point 1.6% cocoyl glycinate (HPLC: standard lauroyl glycinate). The theoretical value for the proportion of cocoyl glycinate at this time point is 17.9%.

The invention claimed is:
1. A method comprising the method steps of
A) providing a mixture comprising an amino acid and an amidamine,
B) reacting the amino acid with an acyl group donor to obtain an N-acylamino acid, and
C) betainization of the amine with a halocarboxylic acid.
2. The method according to claim 1, wherein the amino acid is selected from the group consisting of peptides, oligopeptides, proteinogenic amino acids, non-proteinogenic aminocarboxylic acids and aminosulphonic acids.
3. The method according to claim 1, wherein the amino acid is selected from the group consisting of sarcosine, methyltaurine, taurine, glycine, alanine, valine and glutamic acid.
4. The method according to claim 1, wherein the amidamine is selected from those of the general formula 1)

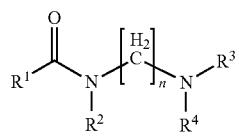

general formula 1)

where $R^1$=hydroxy-substituted, optionally mono- or polyunsaturated alkyl or alkaryl radicals comprising 5 to 29 carbon atoms,
where $R^2$=H or alkyl radical comprising 1-3 carbon atoms,
where $R^3$ and $R^4$=mutually independent, identical or different H or alkyl radicals comprising 1 to 6 carbon atoms, and
n=1 to 6.
5. The method according to claim 1, wherein A) further comprises a trialkylamine selected from those of the general formula 2):

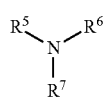

general formula 2)

where $R^5$=hydroxy-substituted, optionally mono- or polyunsaturated alkyl or alkaryl radicals comprising 6 to 30 carbon atoms,
$R^6$ and $R^7$=mutually independent, identical or different alkyl radicals comprising 1 to 6 carbon atoms.
6. The method according to claim 1, wherein the mixture provided in method step A) further comprises water and the water for carrying out method step B) is reduced to a content of below 0.5% by weight wherein the % by weight refers to the sum total of amino acids, amidamine and water.
7. The method according to claim 1, wherein in method step B) an acyl group donor is used selected from acyl group donors which provide an acyl group selected from the group of acyl groups of fatty acids selected from natural fats and oils.
8. The method according to claim 1, wherein method step B) is carried out in a temperature range from 80° C. to 160° C. in a pressure range from 1 to 3000 mbar.
9. The method according to claim 1, wherein the components amino acid, amine and the sum total of the acyl groups of the acyl group donors are used in a molar ratio of from 1:100:1 to 100:1:100.
10. The method according to claim 1, wherein the halocarboxylic acid is chloroacetic acid.
11. The method according to claim 1, wherein the halocarboxylic acid is selected from the group consisting of chloroacetic acid and chloropropionic acid.
12. The method according to claim 1, wherein method step C) is carried out maintaining a pH in the range of 7 to 13.
13. The method according to claim 1, wherein method step C) is carried out in a temperature range from 40° C. to 120° C.
14. The method according to claim 1, wherein method step C) is carried out up to a free amine content of below 0.5% by weight, wherein the % by weight refers to the total amount of amine used in method step A).
15. The method according to claim 1, wherein water is added as solvent in method step C, in particular in a weight ratio of water to amine of from 1:0.01 to 0.01:1.
16. The method according to claim 4, wherein
$R^1$=hydroxy-substituted, optionally mono- or polyunsaturated alkyl or alkaryl radicals comprising 7 to 17 carbon atoms,
where $R^2$=H
where $R^3$ and $R^4$=methyl and
n=3.
17. The method according to claim 5, wherein
$R^5$=hydroxy-substituted, optionally mono- or polyunsaturated alkyl or alkaryl radicals comprising 8 to 18 carbon atoms,
$R^6$ and $R^7$=methyl.
18. The method according to claim 1, wherein the mixture provided in method step A) further comprises water and the water for carrying out method step B) is reduced to a content of below 0.1% by weight wherein the % by weight refers to the sum total of amino acids, amidamine and water.
19. The method according to claim 1, wherein method step B) is carried out in a temperature range from 110° C. to 150° C. in a pressure range from 900 to 1100 mbar.

20. The method according to claim 1, wherein the components amino acid, amidamine and the sum total of the acyl groups of the acyl group donors are used in a molar ratio of from 1:2:1 to 2:1:2.

* * * * *